US010039488B2

(12) United States Patent
Hermann et al.

(10) Patent No.: US 10,039,488 B2
(45) Date of Patent: Aug. 7, 2018

(54) SYSTEM AND METHOD TO DETERMINE TISSUE COMPRESSION (75) Inventors: Sonja Hermann, Dublin (IE); Richard Reilly, Dublin (IE)

(73) Assignee: Provost, Fellows, Foundation Scholars and the other members of the Board of the College of the Holy and Undivided Trinity of Queen Elizabeth, near Dublin, Dublin (IE)

( * ) Notice: Subject to any disclaimer, the term of this patent is extended or adjusted under 35 U.S.C. 154(b) by 942 days.

(21) Appl. No.: 14/343,953

(22) PCT Filed: Sep. 10, 2012

(86) PCT No.: PCT/EP2012/067677
§ 371 (c)(1),
(2), (4) Date: Jul. 23, 2014

(87) PCT Pub. No.: WO2013/034775
PCT Pub. Date: Mar. 14, 2013

(65) Prior Publication Data
US 2015/0230747 A1 Aug. 20, 2015

Related U.S. Application Data (60) Provisional application No. 61/532,856, filed on Sep. 9, 2011.

(51) Int. Cl.
*A61B 5/00* (2006.01)
*A61B 5/103* (2006.01)
(Continued)

(52) U.S. Cl.
CPC ........... *A61B 5/447* (2013.01); *A61B 5/0205* (2013.01); *A61B 5/026* (2013.01); *A61B 5/1036* (2013.01);
(Continued)

(58) Field of Classification Search
CPC combination set(s) only.
See application file for complete search history.

(56) References Cited

U.S. PATENT DOCUMENTS 4,117,798 A * 10/1978 Cornelius ............... B05C 7/02
118/423
4,682,608 A * 7/1987 De Rigal ............ A61B 5/0051
600/587
(Continued)

OTHER PUBLICATIONS

"Notification of Transmittal of the International Search Report and the Written Opinion of the International Searching Authority, or the Declaration," International Filing Date: Sep. 10, 2012, International Application No. PCT/EP2012/067677, Applicant: The Rovost, Fellows, Foundation Scholars, and . . . , dated Feb. 20, 2013, pp. 1-11.

*Primary Examiner* — John R Downey
*Assistant Examiner* — Shirley Jian
(74) *Attorney, Agent, or Firm* — Cesari and McKenna, LLP (57) ABSTRACT The invention describes a system and method how tissue compression can be measured continuously in a non-contact way to provide a low cost, patient/user specific measurement system. The method may be used to inform existing and future pressure relief mattress systems. The invention may also be used for any application either in conjunction with another system or on its own to measure tissue compression. In another embodiment the invention can be used for measuring any type of compression of a compressible material, for example compression of viscoelastic foam or other materials. The invention may also be used to make inferences about the changes of blood flow at site of measurement.

15 Claims, 8 Drawing Sheets (51) Int. Cl.
*A61B 5/0205* (2006.01)
*A61B 5/026* (2006.01)
*A61B 19/00* (2006.01)

(52) U.S. Cl.
CPC .......... *A61B 5/6892* (2013.01); *A61B 5/7246* (2013.01); *A61B 5/7275* (2013.01); *A61B 5/7278* (2013.01); *A61B 5/7282* (2013.01); *A61B 5/742* (2013.01); *A61B 19/46* (2013.01); *A61B 2019/465* (2013.01); *A61B 2562/0247* (2013.01)

(56) References Cited

U.S. PATENT DOCUMENTS

| | | | |
|---|---|---|---|
| 4,777,599 A * | 10/1988 | Dorogi | A61B 5/0051 600/552 |
| 4,838,275 A | 6/1989 | Lee | |
| 6,790,186 B1 * | 9/2004 | Field | A61B 5/103 600/587 |
| 8,758,271 B2 * | 6/2014 | Hunter | A01G 7/00 600/587 |
| 8,821,418 B2 * | 9/2014 | Meger | A61B 5/0002 600/595 |
| 9,265,461 B2 * | 2/2016 | Hunter | A61B 5/0053 |
| 9,333,060 B2 * | 5/2016 | Hunter | A61C 17/02 |
| 9,585,666 B2 * | 3/2017 | Yu | A61B 17/1128 |
| 2004/0106893 A1 * | 6/2004 | Hunter | A61B 5/0051 604/66 |
| 2009/0056427 A1 * | 3/2009 | Hansma | A61B 5/0053 73/82 |
| 2011/0112442 A1 | 5/2011 | Meger et al. | |
| 2011/0144455 A1 | 6/2011 | Young et al. | |

* cited by examiner

SYSTEM AND METHOD TO DETERMINE TISSUE COMPRESSION

CROSS-REFERENCE TO RELATED APPLICATIONS

The present application is the National Stage of International Application No. PCT/EP2012/067677, filed on Sep. 10, 2012, which claims priority from U.S. provisional patent application No. 61/532,856 filed on Sep. 9, 2011, the disclosure of both of which should be understood to be incorporated into this specification.

FIELD OF THE INVENTION

The invention provides a system and method to determine compression. In particular the invention relates to a system and method to determine tissue compression and/or compression of a material.

BACKGROUND TO THE INVENTION

Tissue compression occurs when people are sitting or lying down for extended periods of time. When tissue is compressed over a longer time it affects blood flow and people are at risk of developing tissue damage as a result of the reduced blood flow in the tissues. Current pressure relief mattress systems are non-specific and timing for pressure relief is only informed by good practice according to the guidelines of the pressure advisory panel. The reason for this somewhat crude "estimation" of adequate pressure relief times for patient movement is that there is at present there is no measurement system, which is able to measure tissue compression using a non-invasive and ideally a non-contact method.

In supine position, mattress elastic properties and the person's body weight itself act on the body tissues, creating forces between mattress and tissue. Tissue compression and interface pressure is thought to considerably contribute to compromised blood flow when lying or sitting for some time. It is also seen as a major factor in the development of pressure ulcers. Naturally people perform what is called "pressure relief movements" which describe body movements to help redistribute pressure on tissues. However in movement compromised or impaired subjects no adequate compensation mechanism is in place. Pressure relief is then carried out manually assisted or by using automated pressure relief mattress systems.

To date treatment and prevention of pressure ulcers consists of frequent load redistribution to maintain tissue viability tissue according to NPUAP-EPUAP guidelines. This is archived by frequent manual movement of the patient, which requires a lot of nursing time and physical effort. Providing automated pressure relief mattresses to patients does assist nursing staff to provide timely pressure relief to the patient, however these systems only offer crude and nonspecific pressure relief. They can only provide to pressure relief based on fixed time intervals as they have no means of determining the current state of blood flow in the patient. Currently no methods exist, which provide an effective means on when to carry out timely pressure relief, consequently pressure relief is either carried out too late or is not adequate.

It is therefore one object of the invention to provide a system and method to measure compression to solve the above mentioned problems.

SUMMARY OF THE INVENTION

According to the invention there is provided, as set out in the appended claims, a method to determine tissue compression of a subject comprising the steps of:
  detecting a ballistic signal passing through tissue material of the subject; and
  measuring changes in the ballistic signal, wherein the measured changes in the signal provide a level of tissue compression.

The invention describes a system and method how tissue compression can be measured in a non-contact way to provide a low cost, patient/user specific measurement system. The method may be used to inform existing and future pressure relief mattress systems. The invention may also be used for any application either in conjunction with another system or on its own to measure tissue compression.

The invention measures the distortion of a ballistic signal occurring when it passes tissue material, for example human tissue. The invention uses the ballistic wave which originates within the human body. As such the ballistic wave passes the tissue from within the body to reach a sensing element placed outside the body as opposed to applying a measuring signal from the outside, i.e. measuring the tissue compression by applying a ballistic signal to the outside of the skin to measure tissue compression. This eliminates the need for a receiver element, which picks up the signal after it passes through and is reflected by the human tissue. While a conventional ballistocardiogram (BCG) method, used to measure heart conditions, aims to filter out distortions, stemming from tissue vibrations, the method is doing the opposite, rather than filtering out the distortions the method, facilitates these distortions, by measuring the change (distortion) in the ballistic wave properties, when passed through a medium.

In one embodiment the invention comprises the step of processing the measured changes with respect to a reference ballistic signal and displaying the level of tissue compression.

In one embodiment the reference ballistic signal is measured from the subject when the tissue material is in an uncompressed state.

In one embodiment the invention comprises the step of analysing the measured changes in the ballistic signal by decomposing the signal into frequency and waveform components.

In one embodiment the invention comprises the step of comparing the frequency and waveform components to identify changes in the signals.

In one embodiment the invention comprises step of identifying fundamental and harmonic signals and calculating the shift in the frequency domain relative to the reference signal indicative of tissue material in an uncompressed state.

In one embodiment the invention comprises the step of calculating a tissue compression index by quantifying changes in frequencies of detected ballistic signals between compressed and uncompressed tissue.

In one embodiment the invention comprises the step of visually displaying the tissue compression index calculated.

In one embodiment the ballistic signal is generated by a human.

In one embodiment the invention comprises correlating the measured changes in the signal with the level of tissue compression of the subject for absolute measurement.

In one embodiment the invention comprises the step of filtering the ballistic signal to extract frequency components of the measured ballistic signals.

In one embodiment the step of filtering uses a band pass or low pass filter.

In one embodiment the invention comprises the step of determining changes in blood flow as a function of the level of tissue compression measured in the subject. It will be appreciated that the method can be used to make inferences about changes in blood flow as caused by tissue compression. The tissue compression can result from a combination of closed off blood vessels in the compressed tissue as well as the redistribution of blood flow which occurs, i.e. blood is redistributed to non-compressed areas of the tissue and as such flow will be increased in those areas. So by tissue compression the blood volume in tissue layers above site of compression is increased further contributing to the tissue compression by the increased volume weight of blood. Thus there is an inverse relationship between blood flow increases in non-compressed tissue regions and tissue compression as such that blood flow in those areas may be inferred by the level of tissue compression. It was demonstrated that when flow was varied i.e. weight on tissue changed this.

In one embodiment the invention comprises the step of calculating an inverse relationship between blood flow increase in non-compressed tissue regions and tissue compression regions from the level of tissue compression.

In another embodiment of the invention there is provided a method to determine compression properties of a material comprising the steps of:
applying a ballistic signal to the material;
applying a force to compress the material; and
measuring changes in the ballistic signal over a period of time; wherein the measured changes in the signal provide compression parameters of the material.

In one embodiment the invention can be used for measuring any type of compression of a compressible material, for example compression of viscoelastic foam or other materials, which have viscoelastic or elastic as compared to plastic properties. In this particular case in the absence of a human ballistic input signal a simulated ballistic input signal may be used instead. Further it can be used in any combination of the above for example to measure tissue and support interface compression combined by using a human or (simulated) ballistic input waveform.

In a further embodiment of the invention there is provided a system to determine compression properties of a material comprising the steps of:
applying a ballistic signal to the material;
applying a force to compress the material; and
measuring changes in the ballistic signal over a period of time; wherein the measured changes in the signal provide compression parameters of the material.

In a further embodiment there is provided a system to determine tissue compression of a subject, said system comprising:
means for detecting a ballistic signal passing through tissue material of the subject; and
means for measuring changes in the ballistic signal, wherein the measured changes in the signal provide a level of tissue compression.

In one embodiment there is provided means for processing the measured changes with respect to a reference ballistic signal and displaying the level of tissue compression.

In one embodiment the reference ballistic signal is measured from the subject when the tissue material is in an uncompressed state.

In one embodiment there is provided means for analysing the measured changes in the ballistic signal by decomposing the signal into frequency and waveform components.

In one embodiment there is provided means for comparing the frequency and waveform components to identify changes in the signals.

In one embodiment there is provided means for identifying fundamental and harmonic signals and calculating the shift in the frequency domain relative to the reference signal indicative of tissue material in an uncompressed state.

In one embodiment there is provided means for calculating a tissue compression index by quantifying changes in frequencies of detected ballistic signals between compressed and uncompressed tissue.

In one embodiment there is provided means for visually displaying the tissue compression index calculated.

In one embodiment the ballistic signal is generated by a human.

In one embodiment there is provided means for correlating the measured changes in the signal with the level of tissue compression of the subject In one embodiment there is provided means for filtering the ballistic signal to extract frequency components of the measured ballistic signals.

In one embodiment the means for filtering comprises a band pass or low pass filter.

In one embodiment there is provided means for determining changes in blood flow as a function of the level of tissue compression measured in the subject.

In one embodiment there is provided means for calculating an inverse relationship between blood flow increase in non-compressed tissue regions and tissue compression regions from the level of tissue compression.

In one embodiment the invention may be used in a wider sense for determining tissue compression at any anatomical site of the body which is in contact with a support or interface surface.

There is also provided a computer program comprising program instructions for causing a computer program to carry out the above method which may be embodied on a record medium, carrier signal or read-only memory.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE INVENTION

In the human body ballistic waves are generated by the mechanical action of the heart and transmitted through the column of blood. These waves have been studied extensively in relation to cardiac events and as such been described and used to make inferences about heart health. The waves are visualized by a method known as Ballistocardiography (BCG). The term "ballistocadiogram" as found in the literature refers to a ballistic wave, its waveform and frequency components as analysed in relation to cardiac events or health.

While the BCG signal specifically provides an output of local heart mechanics the invention makes use of the fact that the ballistic wave can be measured at any site/location of the body. When measured at a particular body site, the wave properties measured by a system are affected by the local conditions at the site of measurement and as such do not directly relate to cardiac events anymore. The ballistic wave is propagated through the body via the blood vessel system of the body and travels in form of a pulse wave.

The present invention makes use the nature of a ballistic wave signal in a human body to provide a method and system to detect (measure) the distortions of the ballistic wave when passed through a medium. In particular the invention makes use of the fact that the ballistic wave is changed when it passes through tissues. To reach the site of measurement the ballistic wave needs to pass through the vessel wall and tissues layers. When the vessel wall and the tissues are compressed the wave will travel through a denser medium, which will affect the composition of the ballistic waveform picked up on the site of measurement. The herein described system and method thus utilizes the ballistic waves in a novel way to measure tissue mechanical properties. In particular the method uses the physical principle of a ballistic impulse (wave) as an input signal, to make inferences about the relative degree of tissue compression as measured by a suitable system. To illustrate the measurement principle the method may be loosely compared to the method of ultrasound, where a sound wave encounters a material with a different density, part of the wave is reflected back to the probe and is detected as an echo. Instead of using an artificially generated sound the ballistotissuegram uses the ballistic signal as input, generated by the human body.

Example Embodiment

Figure 1:
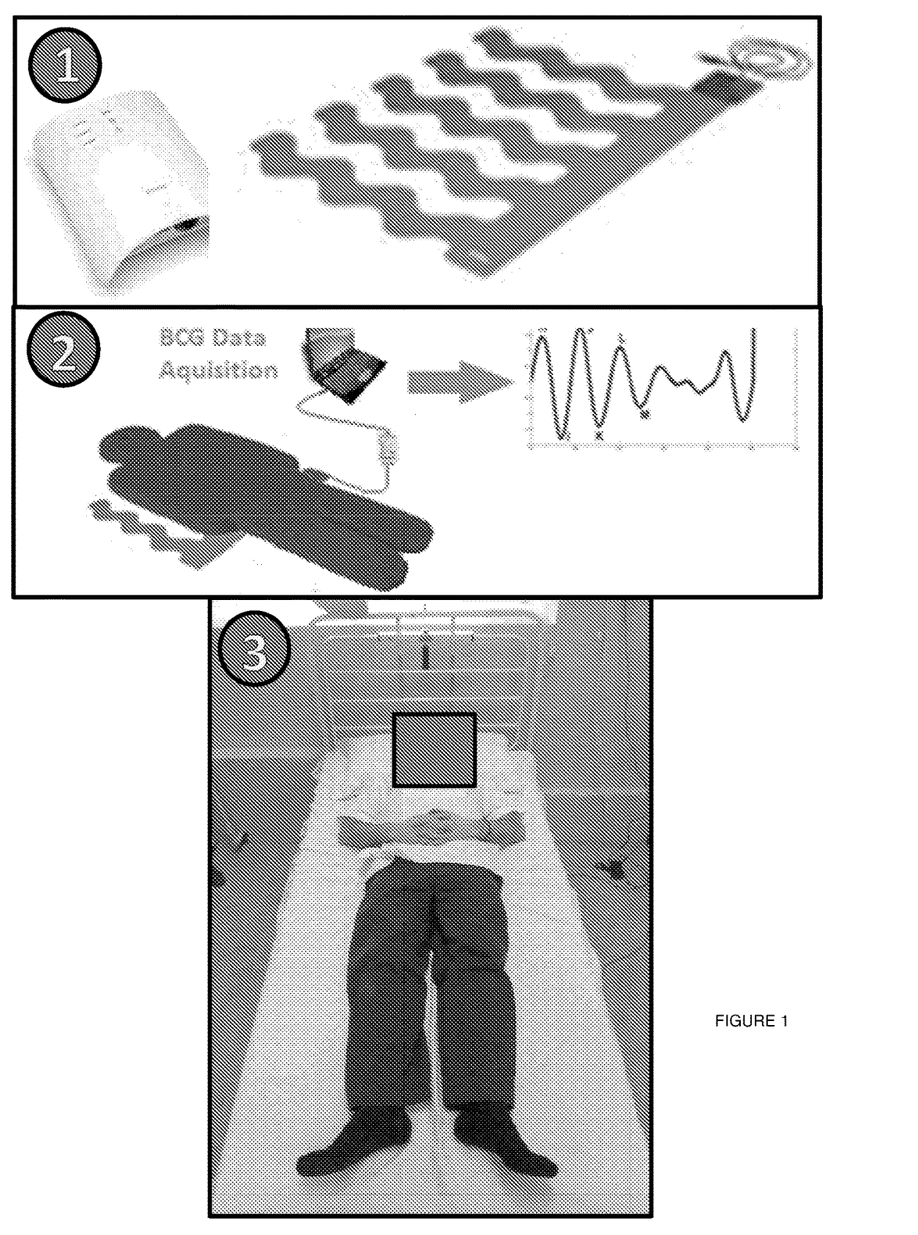
FIG. 1: Experimental set-up. in 1 an EMFI sensor mat is shown with the signal acquisition box, in 2 the positioning of the mat in relation to the heart and the generated waveform, in 3 a subject lying on the hospital bed, is shown.
Figure 2:
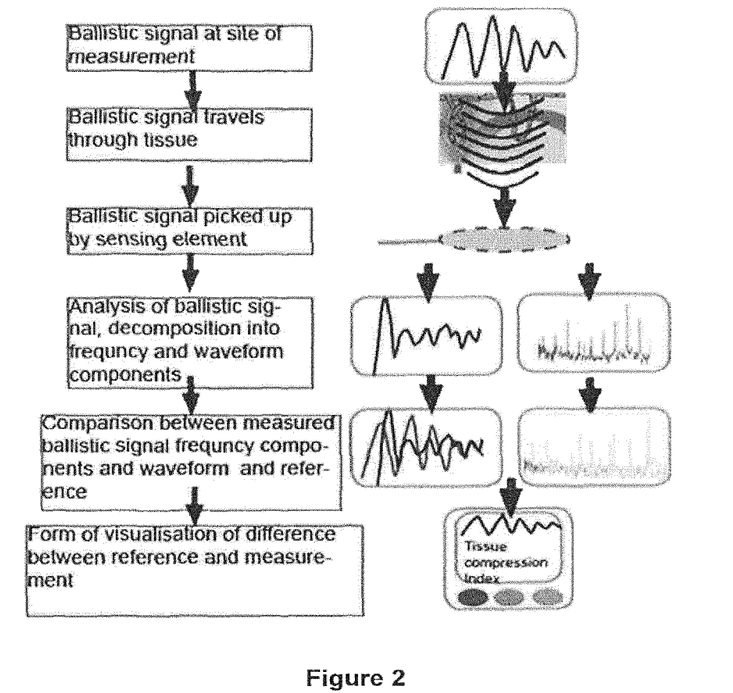
FIG. 2: illustrates a flowchart and schematic of the invention in operation.

The system configured to implement the present invention is shown in FIG. 1 to measure tissue compression using the Ballistotissuegram. FIG. 1 illustrates an experimental set-up according to one embodiment of the invention. In section 1 the EMFI sensor mat is shown with the signal acquisition box, in 2 the positioning of the mat and the generated waveform, in three a subject lying on the hospital bed, is shown. FIG. 2 illustrates flowchart and schematic of the invention in operation.

Step 1—Input:

The measurement system uses the ballistotissuegraph signal as an input signal. Polyolefin material (EMFIT®) may be used, being a suitable thin, flexible, non-contact and cleanable sensor material to pick up the ballistotissuegraph signal, being sensitive to mechanical vibrations. However any other sensor technology, which is sensitive enough to pick up small mechanical vibrations may be used instead. The ballistic signal travels through tissue material of the subject and the signal is sensed by the sensing element.

Step 2—Processing:

A reference ballistotissuegraph signal is taken at the beginning of a measurement period. During the duration of the signal acquisition period the frequency content at suitable time intervals and waveform and signal amplitude are continuously extracted from the ballistotissuegraph signal. The ballistotissuegraph signal has a natural frequency, which is at approximately 1 Hz. This frequency can vary between different people and is thus person specific.

Step 3—Output:

The system output will provide a relative tissue compression index, which may be calculated and visualised in a suitable way by comparing the difference between the reference fundamental/resonance frequencies and the fundamental/resonance frequencies measured at suitable time intervals. The higher the tissue compression and thus the compromise on the blood flow the more the natural and resonance frequencies shift when compared to the reference frequency measured at the beginning A suitable tissue compression index can be expressed for example as the percentage change of the measures signal from the reference signal on a graphical user friendly interface adapted to the needs of the user (clinician, nurse or consumer). Any other means of demonstrating the change between reference signal and test signal may be implemented as well.

Figure 3:
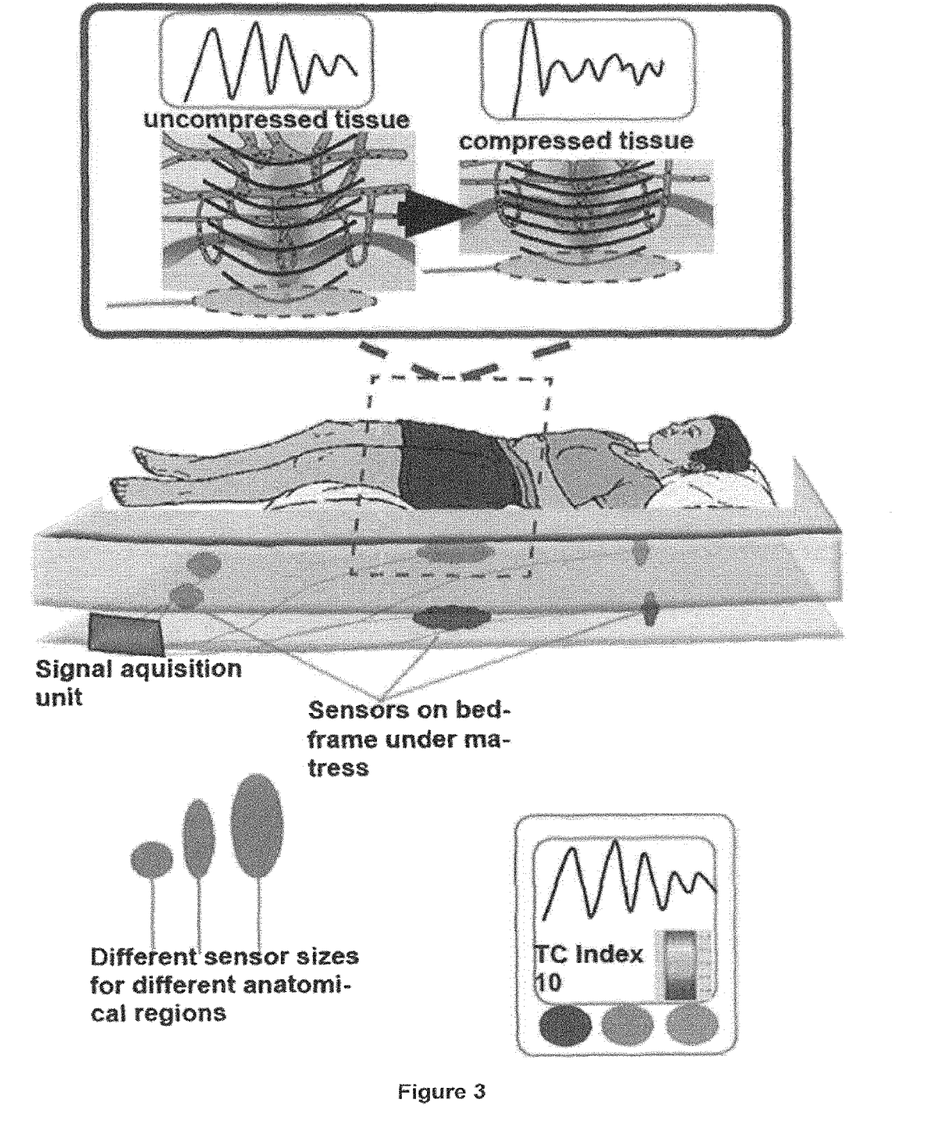
FIG. 3 is a more detailed view of the experimental set up of FIG. 1 showing the signal associated with normal tissue and compressed tissue.

FIG. 3 is a more detailed view of the experimental set up of FIG. 1 showing the signal associated with normal tissue and compressed tissue. The reference signal for the degree of tissue compression will be taken shortly after someone has sit or lied down. This reading is providing the tissue status at the beginning of measurement via a GUI and acts as reference signal. Continuous measurement will provide the degree as to which the reference signal is changing over time via the same GUI. With increasing tissue compression the signal frequency components change. Through a series of experiments it has been demonstrated that increasing tissue compression changes the amplitude of the ballistic signal and at the same time produces a shift in the peak frequencies of the signal. Translated into a suitable GUI representation, the change the reference signal to the measured signal is provided to the user enabling the user to plan for interventions, when increased tissue pressure is reported by the GUI.

This example measurement system provides as an output the relative tissue compression. Moreover when used with a suitable reference, the system can be calibrated to enable absolute measurement. The system is optimised for continuous measurement, but can also be used to take samples at certain times. The material which is used as material for the sensor can be placed under the support surface when the support surface is foam or a medium which transmits the waves. As such the ballistic waves will also enable the measurement of the compression of the support surface. The system can thus give a relative measurement of the human tissue compression, and also give a relative measurement of the foam compression of the support material. Further the output can be visualised on a suitable graphical user interface (GUI).

Experimental Results

A number of experiments were performed to validate the method. Previous research identified and tested a suitable physiological variable. The choice of sensor technology depends on the constraints of the envisioned product development. The "ballistotissuegraph" was identified and described. Previous research has shown the ballistic wave signal to be sensitive to the anatomical recording site and body position (Study 1). In vivo experiments (Study 2) show ballistic wave signal sensitivity to tissue compression. Study 3 suggested the leg ballistic wave signal can be described as a volume pulse wave in its origin.

In the fourth research study to support the development of the method of the ballistotissuegraph, it was attempted to reproduce the results of the in vivo measurements. The aim was to be able to show that by combining simulation of different degrees of compromised blood flow with simulating the associated tissue compression an output may be produced, which is similar to the signal measured in vivo previously, thus demonstrating that in vivo measuring ware able to pick up changes in tissue. A small weight simulated the tissue compression along with the weight of the tissue itself. In the experiments both methods are used to simulate different degrees of compromised blood flow in the compressed tissues.

To understand and explain the vivo testing results (the origin of the waveform and associated frequency contents) a simulation test circuit consisting of a circulation model with anatomical properties was designed.

Materials and Methods

Circulation Model:

A circulation model was used to simulate the human circulatory system. It consisted of a pneumatic pump, and passive mechanical valves, acting as artificial heart with heart valves, an air chamber to simulate different hydrostatic pressures, and collapsible and elastic tubes, to simulate the arterial and venous system. Saline as used as systemic fluid. This set-up allowed to simulate fluid pressures with different pulse pressure (PP) and flow rates (Q). The pump was mounted onto a table. Separate melanin boards, resting on a support frame, independent of the table, the pump was mounted on, supported the remaining circulation model to minimise the influence of the pumps mechanical vibrations on the rest of the test circuit.

Simulation of Compressed Tissue and Compromised Blood Flow:

A two-step method was chosen to generate a realistic representation of the in vivo situation. The model is based on the assumption that the vessels closer to the skin are compressed first and are more compromised in their blood flow than vessels further away from the support surface. The microcirculation part of the simulated circuit represented the compressed vessels. It is assumed that those vessels will not contribute to the ballistic signal much as they are compressed and as such do not exhibit much ballistic properties. It is further assumed that the vessel(s), which will contribute the most to the signal, will be in uncompressed or less compressed tissue layers. This vessel is simulated in the tissue part, which allows to test for the distortions of the signal when passed through the tissue.

Compressed Tissue Simulation:

A 0.5% agarose solution was used to simulate the body tissue. Agarose solution was poured into a container with dimensions and cured for two hours. An elastic tube (d=8 mm, l=100 mm), previously developed to replace a leg artery in bypass procedures, was place at 40 mm distance from the support surface before curing, to simulate the human leg arterial properties. A weight of 100 g was put on top of the tissue.

Simulation of Microcirculation Vessel Compression:

The compression of the vessels was simulated separately. The microcirculation was simulated by 4 small tubes branching off the main circulation. Two branches had a tube diameter of 8 mm and two had one of 5 mm. Each of these branches could be closed off separately thus only allowing flow through the open tubes. Branch 4 was connected to the simulated tissue. This way the systemic fluid will flow from branch 4 to the tissue and back to branch 4.

Signal Acquisition:

Highly sensitive elastic ferroelectret film sensor, oval shaped sensor with a measurement area of ca. (EMFIT® 19 mm R-Series) was used for ballistic signal acquisition. Flow was recorded using a flowmeter. Pressure was recorded before and after tissue.

Data Treatment:

Ballistic signal, pressure pulse and flow rate were recorded, synchronized (NI my-daq), saved in lvm format (Labview 9.0.) and analysed (Matlab2007) for the ballistic waveform frequency components. Power spectral density of the ballistic signal was calculated using the welch method in matlab.

Procedure:

Flow rate was set to a desired value at the beginning of measurement. Flow rate, systolic and diastolic pressure and heart frequency was recorded at the beginning of each measurements. Two set of trials were recorded, in which the distance of the artificial vessel to the sensor was varied. Trial one recorded the ballistic waveform according to the experimental set-up above with the sensor placed under the simulated tissue mass. A 100 g weight was placed on top of tissue. Sensor distance to the artificial vessel was 40 mm.

In trial 2 the sensor was placed on top the simulated tissue mass, with the weight now being now placed on top of the sensor. Sensor distance was 20 mm.

Thus sensor distance to ballistic signal, flow rate (l/min.) and the number of vessels available for flow were varied (see table 1). Flow rates in trial 1 were varied according to table 1. Flow rates for trial two were kept more or less constant. Please not that due to the physiological properties of the circuit, it was not possible to exactly replicate the same flow rate. Only approximate replications i.e. constant flow rate in trial 1 were possible.

TABLE 1

Measurement combinations

| Distance to sensor | Flow rates (l/min.) | No. of vessels closed |
|---|---|---|
| 20 mm | 0.772 | 0 |
|  | 0.797 | 1 |
|  | 0.806 | 1, 2 |
|  | 1.086 | 1, 2, 3 |
| 40 mm | 0.76 | 0 |
|  | 0.775 | 1 |
|  | 0.649 | 1, 2 |
|  | 0.8 |  |
|  | 0.76 | 1, 2, 3 |
|  | 1.060 |  |
|  | 1.159 |  |

Results

Power spectral density of the ballistic signal was calculated using the Welch method. The flow rate was kept constant to approximately 0.76 l/min.

Figure 4:
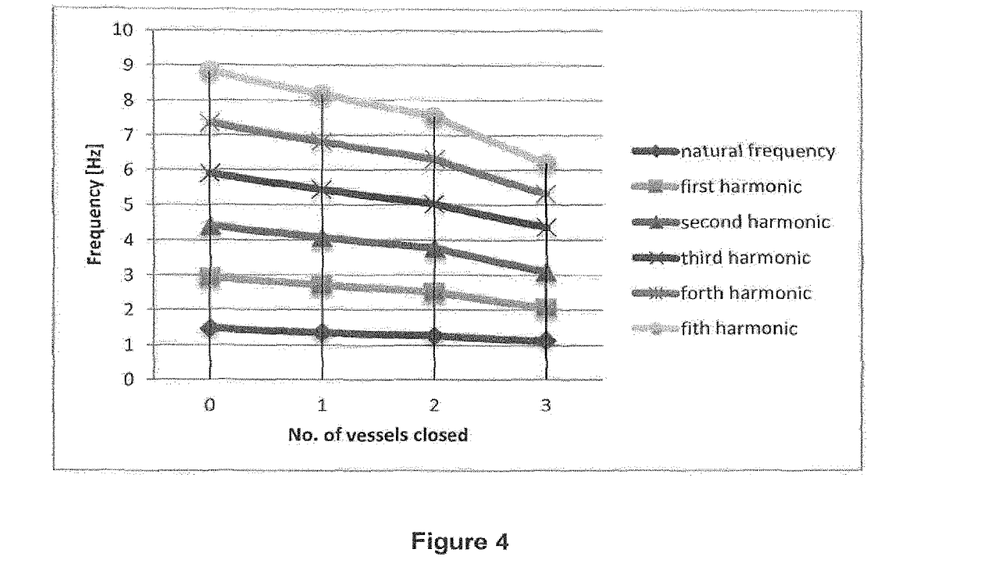
FIG. 4: illustrates a frequency/resonance frequencies response to the number of microcirculation vessels closed off, when the sensor was placed under the simulated tissue in a distance of 40 mm to the replacement artery, which was embedded in the tissue.

Trial 1: Sensor Recorded Ballistic Signal Under Tissue, Distance to Sensor 40 mm:

The peak frequency and associated resonance frequencies were plotted against the number of vessels in the microcirculation, which were closed off. The flow rate was kept constant at 0.76 l/min. FIG. 4 illustrates a frequency/resonance frequencies response to the number of microcirculation vessels closed off, when the sensor was placed under the simulated tissue in a distance of 40 mm to the replacement artery, which was embedded in the tissue.

Trial 2: Sensor Recorded Ballistic Signal on Top of Tissue, Distance to Sensor 20 mm:

The peak frequency and associated resonance frequencies were plotted against the number of vessels in the microcirculation, which were closed off. The flow rate was kept constant at 0.775 l/min.

Figure 5:
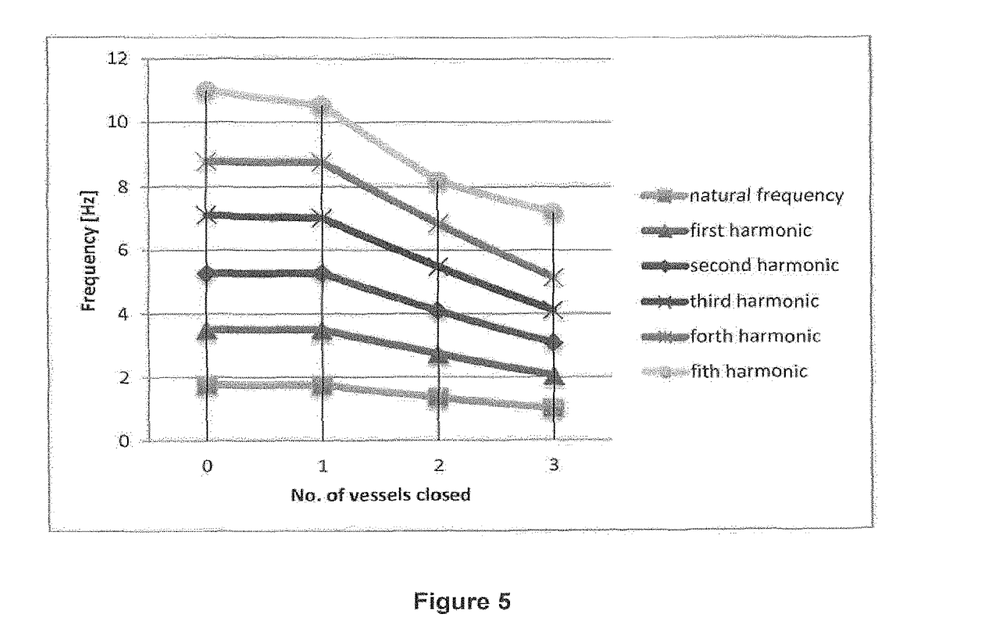
FIG. 5: Frequency/resonance frequencies response to the number of microcirculation vessels closed off, when the sensor was placed on top of the simulated tissue with 20 mm distance to the replacement artery, which was embedded in the tissue.

FIG. 5 illustrates a Frequency/resonance frequencies response to the number of microcirculation vessels closed off, when the sensor was placed on top of the simulated tissue with 20 mm distance to the replacement artery, which was embedded in the tissue. In trial two the flow rate was varied for conditions: 1,2 vessels closed off and 1,2,3, vessels closed off.

Figure 6:
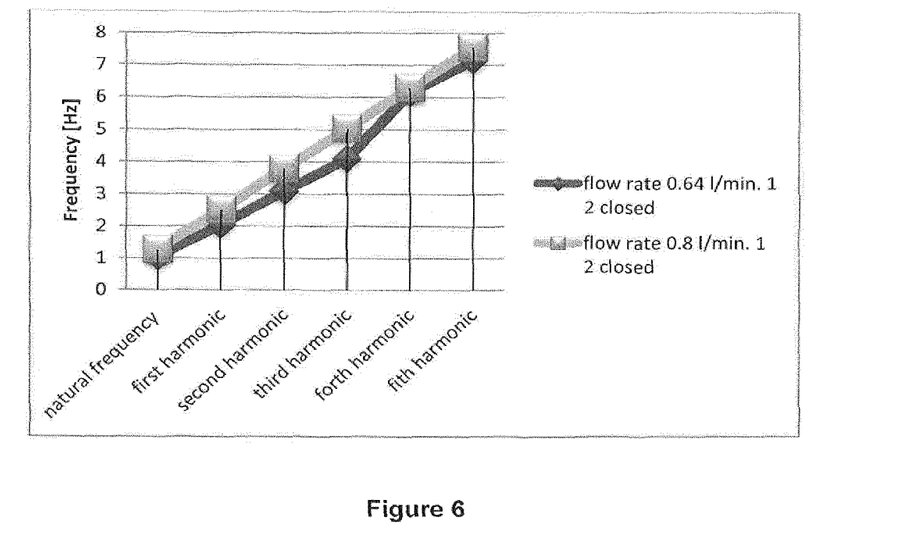
FIG. 6: Dependency of the ballistic signal frequency content on flow rate, 2 microcirculation vessels closed.
Figure 7:
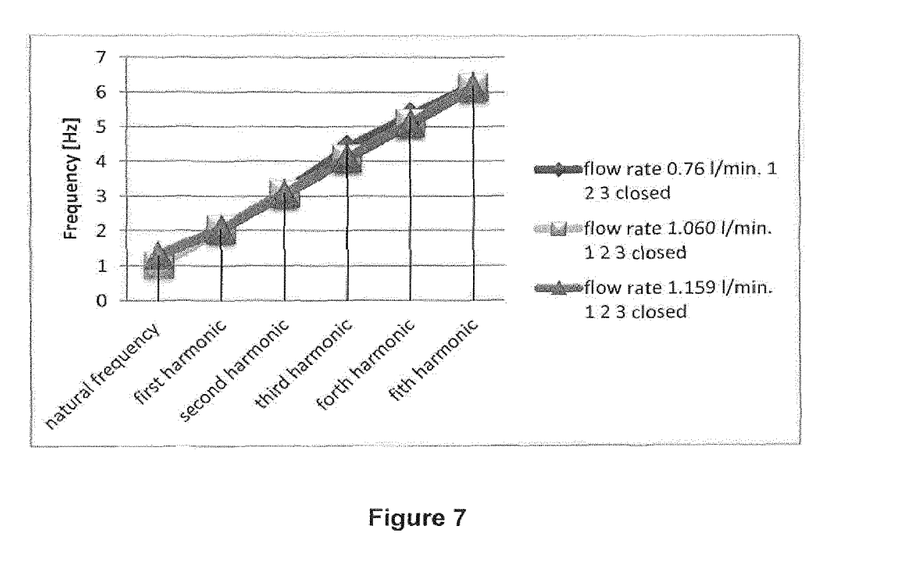
FIG. 7: Dependency of the ballistic signal frequency content on flow rate, 3 microcirculation vessels closed.

FIGS. 6 and 7 show the response of the ballistic signal to flow rate changes. FIG. 6 shows the dependency of the ballistic signal frequency content on flow rate as increased as a result of tissue compression, with two microcirculation vessels closed. FIG. 7 shows the dependency of the ballistic signal frequency content on the flow rate, three microcirculation vessels closed as increased as a result of tissue compression.

The results clearly show that with a longer distance of the vessel to the sensor the natural and resonance frequencies of the ballistic signal are lower as when the sensor was closer to the signal.

FIGS. 5 and 6 shows a clear correlation between the degree of occlusion (number of vessels occluded) and frequency content of the ballistic signal. The more vessels are occluded the lower the fundamental and resonance frequencies of the ballistic signal.

When flow rate was increased from 0.6 to 0.8 l/min with two vessels occluded, the fundamental and resonance frequencies of the ballistic signal increased. When flow rate was increased from 0.76 to 1.060 and further to 1.159, with three vessels occluded, the fundamental and resonance frequencies of the ballistic signal decreased slightly. This can be explained by the physiology of the simulated system in particular the viscoelastic properties of the simulated vessel. When the flow rate is increased in the two vessels condition the pressure remains the same, this pressure also remains when flow rate is 0.76 l/min. with the three vessels condition. However when flow rate in the three vessel occlusion condition is further increased the pressure rises approx. 15%, which affects the viscoelastic properties of the simulated vessel recorded. With increased pressure the fundamental and resonance frequencies are lower. In condition three, both the increased flow rate and the occlusion of three instead of two vessels contributed to a higher pressure. This is in accordance with the results of the second condition (varying vessel occlusion). With increasing number of vessels occluded the ballistic signal frequency content also decreases. Thus with increasing vessel occlusion the blood volume in the remaining vessels increases increasing flow and thus pressure on the vessels walls. By more blood volume flowing through the same vessels the weight of this increased blood volume increases the pressure on the underlying tissue, thereby compressing this to a greater extent, consequently a shift to the lower frequencies in the spectrogram was observed. Above results thus can serve to demonstrate, what may occur physiologically when tissue is compressed and how the redistribution of blood from compressed to uncompressed vessels increase tissue pressure even more and as such can be seen to contribute to tissue compression. Thus it may be concluded that the ballistotissuegraph method is sensitive to tissue compression and its associated changes.

By using an artificial artery, which was designed to replace human leg arteries the waveform was closely replicated as it was recorded in the in vivo experiments. The experimental set-up thus allowed for manipulation of the number of vessels, which were occluded (closed off) and the flow rate, both of which are altered when tissue compression occurs. It was demonstrated that there is a linear relationship between the number of vessels occluded and the frequency content of the ballistic wave. This insight and knowledge can be used to inform the analysis of the ballistic wave when used to assess tissue compression. Both the increase in vessel pressure (increases vessel stiffness) and the weight on the tissue, thereby compressing it, will contribute to change the medium, which the ballistic wave has to travel though. Thus a general increase in stiffness of vessel wall and tissue will affect the frequency contents of the signal, where with higher tissue compression the frequency spectrum shows lower frequencies.

In another embodiment the invention provides a method and system to detect changes in blood flow associated with increases in interface pressure and which is related to tissue compression. This parameter can be used to inform a system which will provide adequate pressure relief to prevent pressure ulcers or provide an alarm system for manual intervention techniques. The invention provides a non-invasive system and method which can detect changes in blood flow attributable to interface pressure acting on the body to compress tissue when a subject or patient is recumbent.

In one embodiment the invention further provides the information necessary for an automated system to output feedback on the adequateness of the pressure relief carried out by a system or manual intervention.

The invention covers the aspect of the diagnosis part of a pressure relief system by combining an acquisition technique, such as a ballistic signal, for detecting a new set of features to infer knowledge about blood flow status in response to tissue compression or interface pressure. It further provides information on effectiveness of pressure relief when performed.

The invention provides a means of non invasive, non contact monitoring of blood flow in the regions of bony prominences. It uses the ballistic signal in a novel way by picking up changes in blood flow at sites of bony prominences. The specificity of change at these locations is quantified using a novel method. The invention can thus inform about critically impeded blood flow and can be used to alarm care personal to move patients or as a diagnosis module to determine timely pressure relief in automated mattress pressure relief systems. The inventors found that the ballistic signal as hereinbefore described can be used as a tool to quantify cardiovascular changes associated with aging to inform pressure ulcer risk assessment in movement-compromised elderly subjects In one embodiment the invention provides specific features which may also be used to infer changes in support surface stiffness i.e. mattress support if a foam mattress is being used as support. Thus the invention describes a method, which can be used to detect changes in mattress stiffness and provide also a method on quantifying how these changes affect local blood flow.

In one embodiment the invention provides a non-invasive method for detecting changes in blood volume at body sites associated with high risk of pressure ulcers by providing a non invasive, low cost acquisition technique, describing a suitable signal sensitive to blood volume changes and specific features therein to entirely describe the blood volume status at any instance in time to infer diagnosis on the blood volume status.

In one embodiment the ballistic wave can also provide information about how the mattress is changing in stiffness, when compressed by body weight over a time period and how the blood flow changes in response to this increased mattress stiffness (=termed interface pressure) when the method is used in conjunction with a foam mattress.

In one embodiment there is provided a system adapted to automatically detect deterioration in blood flow with increasing interface pressure and is able to provide feedback on the blood perfusion status. The system is further adapted to assess the amount of mattress compression for each individual subject and is able to relate increases in mattress stiffness, when a foam support surface is used as mattress, to the extent of compromised blood flow. This method may be used to build a module which interfaces with existing mattress pressure relief systems or operate on its own to provide timely feedback if blood flow has been compromised to serve as prevention and warning system in prevention and treatment of pressure ulcers.

Further the invention can be used to facilitate above described method to assess the how well a specific foam surface is suited to its specific user, by providing means of assessing how mattress stiffness or changes affect blood flow and make inferences if blood flow is sufficient or (critically) compromised.

It will be appreciated that the method described in this invention is not restricted to measuring blood volume changes at sites of increased risk of pressure ulcers but may be used at any point in the circulation, where it is desirable to detect changes in blood volume. It may be used to detect those changes not only in supine position but also while seated and thus may also serve as the basis of a warning system to ensure adequate frequency of body movement.

The added functionality of using the method to assess changes in the degree of compression of the foam support will open venues to develop systems, which enable truly personalized foam support surfaces, for bedding, seating cushions, wheelchair cushions and any other foam based support surfaces. Currently there is no known non-contact method, which is able to assess foam compression, while a person sits or lies on a foam support surface i.e. mattress or seating cushion. This added functionality will enable a personalised seating and bedding and will provide a method to seating and bedding manufactures to customise their products to the individual consumer. Thus this method may be used on its own to enable personalisation of foam support surfaces. This would for the first time enable to truly customise for example foam cushions for wheelchair users, by enabling to identify the degree of foam compression at various areas of the foam cushion. With this knowledge truly optimised pressure relief mattresses and foam cushions may be developed or manufactured or customized, not only for the rehabilitation market but also the general consumer market.

Thus far no method can provide this functionality. Current practise in optimising cushions and mattresses for wheelchair users and older persons with high risk of pressure ulcers is based on trial and error, having the persons feedback as the only means of optimization besides the output of pressure sensing systems if available (pressure sensing systems are very costly). However pressure sensing systems only provide information on the pressure between the support surface and the seat, while the method described here provides a means to gain insight in the compression of the foam and is able to assess how the degree of foam compression affects blood flow. Further this method would enable adjustable support surfaces, which respond to the users need, i.e. degree of tissue compression. There is a large market, which would benefit from the present invention, enabling product innovation using this method, for example:

Office seating
Airline seating
Automotive seating
Specialized seating
All mattress support surfaces or foam support surfaces intended for reclined use It will be appreciated that the figures and description referred herein refers to a ballistic signal that naturally occurs in the human body due to heart beat and blood flow and how the invention uses measurement of the ballistic signal at different sites in the body as the ballistic signal propagates through the body to determine tissue compression or material compression. This should not be confused with a known Ballistocardiogram signal that describes the different phases of the heart mechanics. In other words the ballistic signal, according to the invention, is sensed at measurement sites other than the heart region, wherever it is desirable to measure tissue compression and associated changes in blood flow and thus may be termed Ballistotissuegram.

Figure 8:
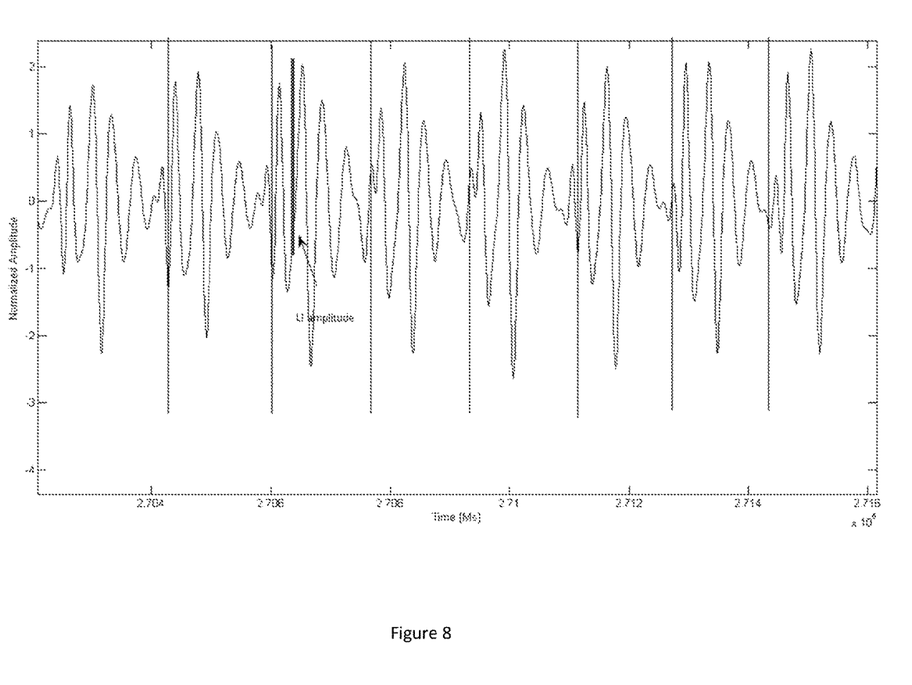
FIG. 8: depicted are several ballistic cycles, the IJ amplitude is shown in one cycle, the IJA is calculated by taking the difference between peak and trough

FIG. 8 illustrates several ballistic cycles, the IJ amplitude is shown in one cycle, the IJA is calculated by taking the difference between peak and trough. Heart beat intervals (HBI) were calculated by extracting the peaks of the QRS complex of the ECG and calculating the time difference between successive peaks. The ballistic signal can be band-pass filtered in the region of 0.5-30 Hz. IJA (acceleration of blood during systole) were calculated by extracting the peaks and previous trough of the filtered data by differencing troughs from peaks.

Figure 9:
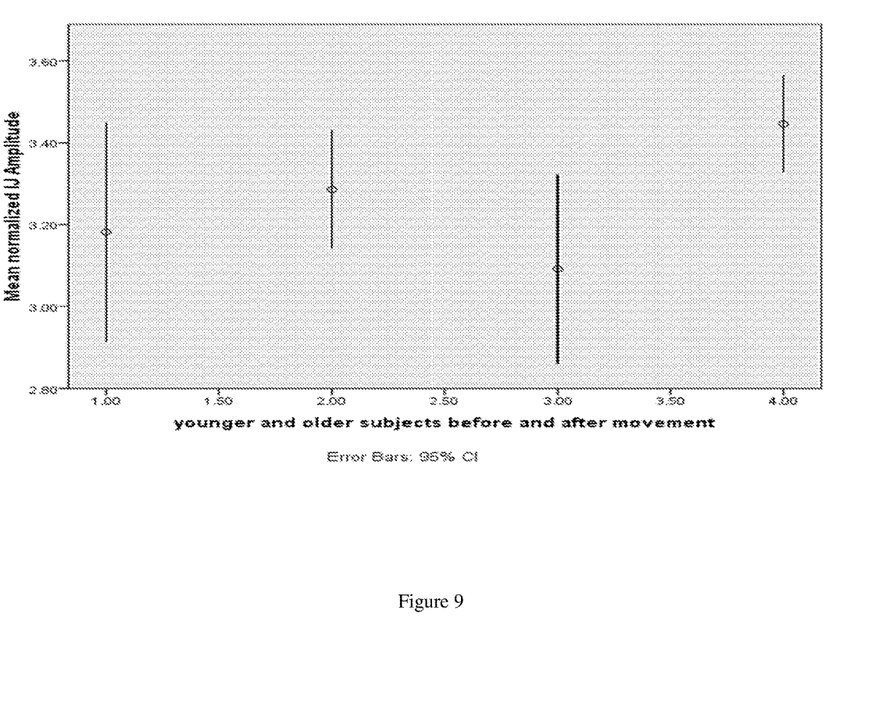
FIG. 9: Mean normalized IJA of ballistic data before and after pressure relief movement.
Figure 10:
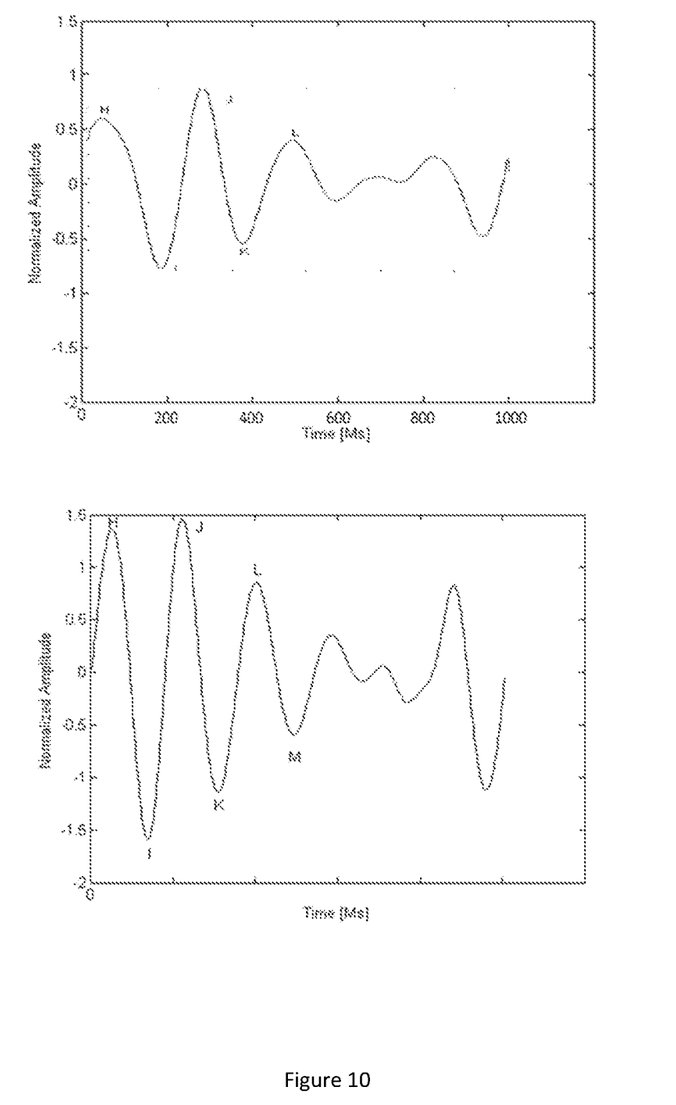
FIG. 10: Average waveforms over 60 min of younger subjects on the left and older subjects on the right.

FIG. 9 illustrates a mean normalized IJA of ballistic data before and after pressure relief movement. FIG. 10 illustrates the average waveforms over 60 min of younger subjects on the left and older subjects on the right. The increase in Amplitude with older subjects is obvious. As shown IJA was significantly higher in older subjects ($Z=-46.08$, $p<0.01$) with decreasing, although non-significant trend over 60 min in all subjects ($F=4.012$, $p=0.058$), No difference was found in the HBI data ($F=12.12$, $p>0.05$). No significant difference ($F=0.949$, $p>0.05$) in IJA was found, while HBI significantly decreased ($F=19.382$, $p<0.01$) when before and after movement was compared.

The consistently higher IJ amplitude with the older subjects over the duration of 60 min may be explained by the changes introduced to the cardiovascular system by aging, such as an increased arterial stiffness and increasing narrowing of the vessel diameter. However no significant difference in heart rate was found when comparing older and younger subjects over the duration of 60 min.

While the ballistic signal showed changes between age groups, no changes irrespective of age could be reported in the ballistic signal amplitude prior to as compared to after the execution of a pressure relief movement. The variable HR was more sensitive to changes seen prior to and after pressure relief with both age groups showing increased HR before and decreased HR after movement.

The ballistic signal accurately captures the changes in the cardiovascular systems, caused by the effects of aging. These changes are not reflected by a concurrent variation in heart rate. Thus changes associated with aging are better represented by the ballistic signal, which provides information about blood acceleration profile, as compared to conventional means such as HR.

It will be appreciated the invention describes a method for measuring changes in blood flow at body sites, which are susceptible to pressure ulcers in a recumbent position. Naturally these areas refer to the ischial tuberosities, is shoulder blades, back of the head, sacrum, calves and heels. There blood flow is compromised due to increased interface pressure between the mattress and patients tissue. Using the principle of a ballistic wave in a new and innovative way, previously used to in the measurement of the Balistocardiogram (BCG), the invention enables to identify and inform when blood flow at sites of bony prominences is critically impeded and thus aims to provide a diagnostic tool which is able to issue a warning to inform when a patient should be moved either manually or by a pressure relief mattress system.

The invention uses the ballistic wave to infer changes in blood flow by applying specifically developed signal processing to the ballistic wave trace, recorded at locations of bony prominences. To do so it uses a combination of sensors made of EMFI", a thin commercially available "quasi-piezoelectric" film, made of polyolefin material. Any other (sensor) material suitable to pick up the ballistic wave may be used. Strategically positioned under the mattress it is used to acquire the ballistic signal trace at sites of bony prominences providing a non-invasive, non-contact method of acquisition, as described with respect to FIGS. 1 to 3.

The BCG is a non-invasive method which records the circulatory mass displacements of the blood, i.e. the change of the center of gravity of the displaced blood volume by action of the heart. The BCG presents information about the summated volume pulses (i.e. local, changing, blood volume contained in a segment of artery) in the cardiovascular system, thus the BGC trace is a summation of volume pulses across the whole body. This invention proposes a new use of the physical principle, which is facilitated in the BCG to make inferences about heart mechanics, using it to infer changes in blood dynamics at local sites of the circulation in particular at sites of bony prominences termed here the ballistic signal. Further a method of analysing the ballistic signal is presented. The ballistic waveform can be divided into the H, I, J, K, L, M, N, using the same naming convention as in the BCG The change in IJK complex is being analysed in this invention along with the changes of the LMN complex. This complex refers to resultant forces, due to the physical properties of body tissues which vibrate for a brief instant after receiving a single blow=blood volume pulse. These after vibrations are expressed in the LMN complex. They change when blood flow becomes more turbulent. The degree of turbulence can be related to the degree of obstruction of flow by applied interface pressure.

This invention analyses the changes of IJK and LMN complex at sites of bony prominences in response to increased interface pressure to infer to changes in blood flow at those sites. A description of one embodiment of how the invention diagnoses compromised blood flow can comprise of the following steps:

The ballistic signal is measured at the chest level noninvasively using EMFI material placed under the mattress. The chest measurement is used as reference ballistic signal.

This chest signal reference trace is compared to a chest reference waveform representing a prone body position. This procedure is carried out to identify patients current body position The ballistic signal is measured at body sites prone to pressure ulcers (bony prominences) using same EMFI material placed under the mattress at dedicated body sites.

Ballistic signal at body sites is recorded

Ballistic signal traces are quantified—amplitude difference in IJK and change in shape in the descending part of the ballistic signal, the LMN complex respectively are determined. Amplitude is determined by peak identification. Shape change of the LMN complex is calculated using non linear techniques (quantification of random component in LMN complex)

The two features are compared against reference trace derived at the beginning of the measurement is stable position.

Diagnosis is made based on change of the two features

Status of local blood flow is outputted

Alarm is issued if blood flow critically compromised

It will be appreciated that the invention has several potential commercial applications, such as:

Can be used in hospitals, homecare and elderly care facilities for patients at risk of pressure ulcers to prevent pressure ulcers from occurring or new pressure ulcers from forming Can be used in research studies to determine changes in blood flow as caused by tissue compression Can inform existing pressure relief mattress systems and improve future systems in their specificity Enables patient specific truly customised pressure relief Provides patient with more independence as system can be used to inform automated systems, no need of a carer is needed to operate the system Consumers and/or institutions which may be interested in developing such products, processes, research tools, or services.

Pressure relief mattress manufacturers and medical device industry

Consumer base for such products, processes, services or research tools

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk.

The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A method to determine tissue compression of a subject comprising the steps of:
   detecting, by a sensor, a ballistic signal generated by a mechanical action of a heart and passing through tissue material of the subject;
   extracting, utilizing a filter, frequency components from the ballistic signal over a period of time;
   measuring changes in the extracted frequency components of the ballistic signal based on a comparison of the extracted frequency components of the ballistic signal with reference frequency components of a reference ballistic signal;
   calculating, based on the comparison, a deviation in a frequency domain between the ballistic signal and the reference ballistic signal;
   producing a parameter based on the calculated deviation, the parameter representing a level of tissue compression of the tissue material from an uncompressed state, wherein a rate of deviation directly relates to the level of tissue compression; and
   displaying, on a graphical user interface, the level of tissue compression.

2. The method of claim 1 further comprising:
   identifying fundamental and harmonic frequency components and calculating a change in the fundamental and harmonic frequency components relative to the reference signal indicative of the tissue material in the uncompressed state.

3. The method of claim 1 further comprising calculating a tissue compression index by quantifying changes in the frequency components of detected ballistic signals between compressed and uncompressed tissue.

4. The method of claim 1 further comprising:
   calculating a tissue compression index by quantifying changes in the frequency components of detected ballistic signals between compressed and uncompressed tissue; and
   visually displaying, on the graphical user interface, the calculated tissue compression index.

5. The method of claim 1 further comprising correlating the changes in the frequency components with the level of compression of the tissue material of the subject.

6. The method of claim 1 further comprising determining changes in blood flow as a function of the level of compression of the tissue material measured in the subject.

7. The method of claim 1 further comprising:
   determining changes in blood flow as a function of the level of compression of the tissue material measured in the subject; and
   calculating an inverse relationship between blood flow increase in non-compressed tissue regions and tissue compression regions from the level of compression of the tissue material.

8. A system to determine tissue compression of a subject, said system comprising:
   a sensor configured to:
      detect a ballistic signal generated by a mechanical action of a heart and passing through tissue material of the subject,
   a filter configured to:
      extract frequency components from the ballistic signal over a period of time;
   processing logic configured to:
      measure changes in the extracted frequency components of the ballistic signal based on a comparison of the extracted frequency components of the ballistic signal with reference frequency components of a reference ballistic signal to calculate a deviation between the ballistic signal and the reference ballistic signal; and
   a graphical user interface configured to display a level of tissue compression based on the calculated deviation, wherein a rate of deviation directly relates to the level of tissue compression.

9. The system of claim 8 wherein the processing logic is further configured to:
   identify fundamental and harmonic frequency components and calculate a change in the fundamental and harmonic frequency components relative to the reference signal indicative of the tissue material in the uncompressed state.

10. The system of claim 8 wherein the processing logic is further configured to calculate a tissue compression index by quantifying changes in the frequency components of detected ballistic signals between compressed and uncompressed tissue.

11. The system of claim 8 wherein
   the processing logic is further configured to calculate a tissue compression index by quantifying changes in the frequency components of detected ballistic signals between compressed and uncompressed tissue; and
   the graphical user interface is further configured to visually display the calculated tissue compression index.

12. The system of claim 8 wherein the processing logic is further configured to correlate the changes in the ballistic signal with the level of compression of the tissue material of the subject.

13. The system of claim 8 wherein the processing logic is further configured to determine changes in blood flow as a function of the level of compression of the tissue material measured in the subject.

14. The system of claim 13, wherein the processing logic is further configured to:
   determine changes in blood flow as a function of the level of compression of the tissue material measured in the subject, and
   calculate an inverse relationship between blood flow increase in non-compressed tissue regions from the level of tissue compression.

15. A method to determine tissue compression of a subject comprising the steps of:
   detecting, by a sensor, a ballistic signal generated by a mechanical action of a heart and passing through tissue material of the subject;
   extracting, utilizing a filter, frequency components from the ballistic signal over a period of time;
   comparing the extracted frequency components of the ballistic signal with reference frequency components of a reference ballistic signal to calculate a deviation between the ballistics signal and the reference ballistic signal;

producing an index value based on the calculated deviation, the index value representing a level of tissue compression of the tissue material, wherein a rate of deviation directly relates to the level of tissue compression; and displaying, on a graphical user interface, the index value representing the level of tissue compression.

\* \* \* \* \*